United States Patent [19]

Kuen

[11] Patent Number: 5,653,842
[45] Date of Patent: Aug. 5, 1997

[54] METHOD OF MAKING A SHAPED ABSORBENT GARMENT

[75] Inventor: David Arthur Kuen, Neenah, Wis.

[73] Assignee: Kimberly-Clark Worldwide, Inc., Neenah, Wis.

[21] Appl. No.: 444,804

[22] Filed: May 19, 1995

Related U.S. Application Data

[62] Division of Ser. No. 841,950, Feb. 26, 1992, abandoned.
[51] Int. Cl.⁶ .............................. B32B 31/00; A61F 13/15
[52] U.S. Cl. ..................... 156/227; 156/292; 604/385.1; 604/358
[58] Field of Search ........................... 156/200, 201, 156/204, 222, 226, 227, 461, 292; 604/385.1, 386, 358

[56] References Cited

U.S. PATENT DOCUMENTS

| | | | |
|---|---|---|---|
| 3,924,627 | 12/1975 | Nystrand | 604/385.1 |
| 4,743,245 | 5/1988 | Lassen et al. | 604/385.1 |
| 4,946,454 | 8/1990 | Schmidt | 604/385.1 |

*Primary Examiner*—John G. Weiss
*Assistant Examiner*—Dennis Ruhl
*Attorney, Agent, or Firm*—Thomas M. Gage

[57] ABSTRACT

A shaped absorbent garment is formed of a shell having an absorbent core positioned between a bodyside liner and a backing sheet. The absorbent core is inwardly folded between a forward terminal point and a rearward terminal point. The forward and rearward terminal points are spaced apart along the central, longitudinal axis of the shell. The shaped absorbent garment includes a narrow crotch section with a vertically-extending channel, and front and rear pockets.

10 Claims, 5 Drawing Sheets

METHOD OF MAKING A SHAPED ABSORBENT GARMENT

This is a divisional application of Application U.S. Ser. No. 07/841,950, filed on Feb. 26, 1992 now abandoned.

BACKGROUND OF THE INVENTION

The present invention relates generally to the field of disposable garments for the absorption and containment of urine and other body exudates. More particularly, the invention pertains to an incontinence garment, a disposable diaper, or the like, that is designed to accommodate fecal material, rapidly absorb fluidic waste, add maintain the wearer dry and comfortable.

Disposable garments for the absorption and containment of urine and other body exudates are generally known in the art. Such disposable garments have found particular utility in the fields of infant care, child care, feminine care, and adult incontinency. Present commercially available disposable garments for such uses are generally unitary, preshaped or prefolded, and comprised of a fluid previous bodyside liner, a fluid impervious backing sheet, and an absorbent material disposed between the bodyside liner and the backing sheet. They generally include some type of attachment system for securing the garment to the body of the wearer.

Various shapes have been devised in an attempt to obtain good body conformance, leakage prevention and comfort. Some prior garments have attempted to obtain body conformity by selecting particular fold geometries and connection points. For example, beneficial fold geometries are disclosed in U.S. Pat. Nos. 4,578,066 to O'Connor and 4,946,454 to Schmidt.

Numerous other patents disclose garments having gathers in the leg regions of the garments. Such patents include U.S. Pat. Nos. 3,426,756 to Romanek; 3,776,233 to Schaar; 4,601,717 to Blevins; 4,623,342 to Ito et al; 4,681,579 to Toussant et al.; and U.K. Published Application No. 2,168,887 to Daugan et al.

Other patents have suggested connecting portions which lie on opposite sides of the longitudinal centerline of the garment. U.S. Pat. No. 3,884,234 to Taylor, for instance, discloses a disposable diaper with a center line extending from the front waistline to the back waistline. The bodyside surface has a first portion on one side of the center line secured to a symmetrical second portion on the opposite side of the center line. The first and second portions are in the form of an arc originating from a location adjacent the center line and extending toward a lateral margin.

Several other patents disclose garments with gathered center portions. For instance, U.S. Pat. No. 2,829,647 to Dexter, discloses a diaper with the central portions of its side edges folded over in wallet fashion and releasably secured by fastening means positioned along the side edges of the diaper. Also, U.S. Pat. No. 4,731,070 to Koci discloses an adult incontinent absorbent article with inwardly-extending folded portions that are secured together. Relatedly, U.S. Pat. No. 3,999,547 to Hernandez discloses a disposable diaper having a box pleated configuration with a central panel, inwardly-extending panels secured thereto, and outwardly-extending panels including abutting inner edges.

A problem in the art is that children or incontinent adults may urinate or defecate in great amounts over a short period of time. The known art does not fully provide for rapid absorption and adequate containment of such discharges. Also, known incontinence garments have not fit closely and snugly in the crotch area, and have thus been somewhat uncomfortable and less than completely effective. What is lacking and needed in the art is a snug fitting, comfortable absorbent garment which more closely fits the wearer in the crotch area, and which can more rapidly absorb and adequately contain urine and fecal discharges.

SUMMARY OF THE INVENTION

The present invention was developed in order to provide a shaped absorbent garment that is comfortable to wear and particularly efficient in absorbing and containing fluidic and fecal waste. A shaped absorbent garment of the present invention generally includes a shell with a central, longitudinal axis. The shell has front and back longitudinally spaced edges. A crotch section is located intermediate the front and back edges, and first and second sides extend between the front and back edges. The shell also includes a bodyside liner, a backing sheet attached to the bodyside liner, and an absorbent core positioned between the bodyside liner and the backing sheet. First forward and rearward contact points of the absorbent core are transversely located between the central, longitudinal axis and the first side. Likewise, second forward and rearward contact points are transversely located between the central, longitudinal axis and the second side. The absorbent core is inwardly folded along the central, longitudinal axis between a forward terminal point and a rearward terminal point. The first and second forward contact points are secured together, and the first and second rearward contact points are secured together.

The invention as described results in a comfortable, close fitting garment having a front pocket, a vertically-extending channel in the crotch section, and a rear pocket. The front pocket is designed to accommodate the genitals of male wearers or comfortably collapse against the body of female wearers. In the crotch section, the vertically-extending channel is designed to rapidly absorb and transport liquid waste away from the wearer. The forward and rearward terminal points are preferably separated by 0.25 to 6.0 inches, more preferably by 1.5 to 4.0 inches, and positioned so that the central, longitudinal fold is formed generally beneath the perineal area of the wearer. The rear pocket is designed and positioned to accommodate fecal waste.

After folding the shell along the central, longitudinal axis, the forward contact points are secured together and the rearward contact points are secured together. Preferably, the forward contact points are located transversely outward from the forward terminal point, and the rearward contact points are located transversely outward from the rearward terminal point.

This aspect results in a shaped garment that provides a more consistent fit than garments with folds that are not secured. Relatedly, the shape of the garment will be different depending upon the transverse position of the contact points. For example, the contact points may be located midway between the central, longitudinal axis and the sides. Alternately, the contact points may be located closer to the sides. In this latter case the crotch section is narrower, and the vertically-extending channel and the front and rear pockets are deeper, than in the former case.

In another aspect of the invention, the shaped absorbent garment includes a shell with an absorbent core, where the absorbent core is inwardly folded along the central, longitudinal axis between a forward terminal point and a rearward terminal point. The absorbent core is also inwardly folded along a pair of forward diverging fold lines that originate at the forward terminal point and extend toward the first and second sides. Further, the absorbent core is inwardly folded along a pair of rearward diverging fold lines that originate at the rearward terminal point and extend toward the first and second sides.

This aspect produces a shaped absorbent garment that closely conforms to the body of the wearer. The forward and rearward diverging fold lines are preferably formed at specified angles. For example, the forward diverging fold lines may each form an angle with the central, longitudinal axis of from about 30 to about 70 degrees, more particularly from about 40 to about 60 degrees. The rearward diverging fold lines each may form an angle with the central, longitudinal axis of from about 40 to about 80 degrees, more particularly from about 55 to about 75 degrees. Desirably, the angle formed between each of the rearward diverging fold lines and the central, longitudinal axis is greater than the angle formed between each of the forward diverging fold lines and the central, longitudinal axis.

In another aspect, the absorbent core includes an acquisition layer formed of a pair of surge sheets. The surge sheets are preferably identical, complementary, and positioned on opposite sides of he central, longitudinal axis. Each surge sheet has a leading section and a trailing section. Most preferably, the leading sections are positioned adjacent the central, longitudinal axis and extend forward of the forward terminal point. Conversely, the trailing sections are spaced apart from the central, longitudinal axis and extend rearward of the rearward terminal point.

This aspect results in rapid absorption and transport of fluidic waste into the garment, because the surge sheets are formed of a material that can accommodate rapid flows of liquids and are positioned to form part of the vertically-extending channel. The leading sections are positioned in the front pocket and provide a dry environment, such as for the male genitals. The trailing sections are not located at the bottom of the rear pocket, where the surge material would not be necessary and would decrease the volume of the rear pocket. Instead, the trailing sections are located adjacent the rear pocket to lessen the chance of sideways leakage. The acquisition layer may optionally comprise a single sheet of material positioned on one side of the central, longitudinal axis or extending over the central, longitudinal axis.

As can be seen from the foregoing comments, it is an object of the present invention to provide a personal absorbent garment that is capable of rapidly absorbing fluidic waste that may be discharged by the wearer.

It is another object of the invention to provide an absorbent garment that is constructed with a rearwardly-positioned pocket to accommodate and properly contain fecal waste.

It is similarly another object of the invention to provide an absorbent garment that is constructed with a forwardly-positioned pocket to accommodate and maintain dry the genitals of male wearers.

It is another object of the invention to provide an absorbent garment that fits the wearer closely and snugly in the crotch area, while also being comfortable to wear.

It is still another object of the invention to provide an absorbent garment that is prefolded and secured together at contact points, so that the garment folding does not change when the garment is worn.

It is yet another object of the invention to provide a shaped absorbent garment for rapidly absorbing body waste, which garment may be efficiently manufactured.

The foregoing and other objects, features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DETAILED DESCRIPTION OF THE PREFERRED EMBODIMENTS

Figure 1:
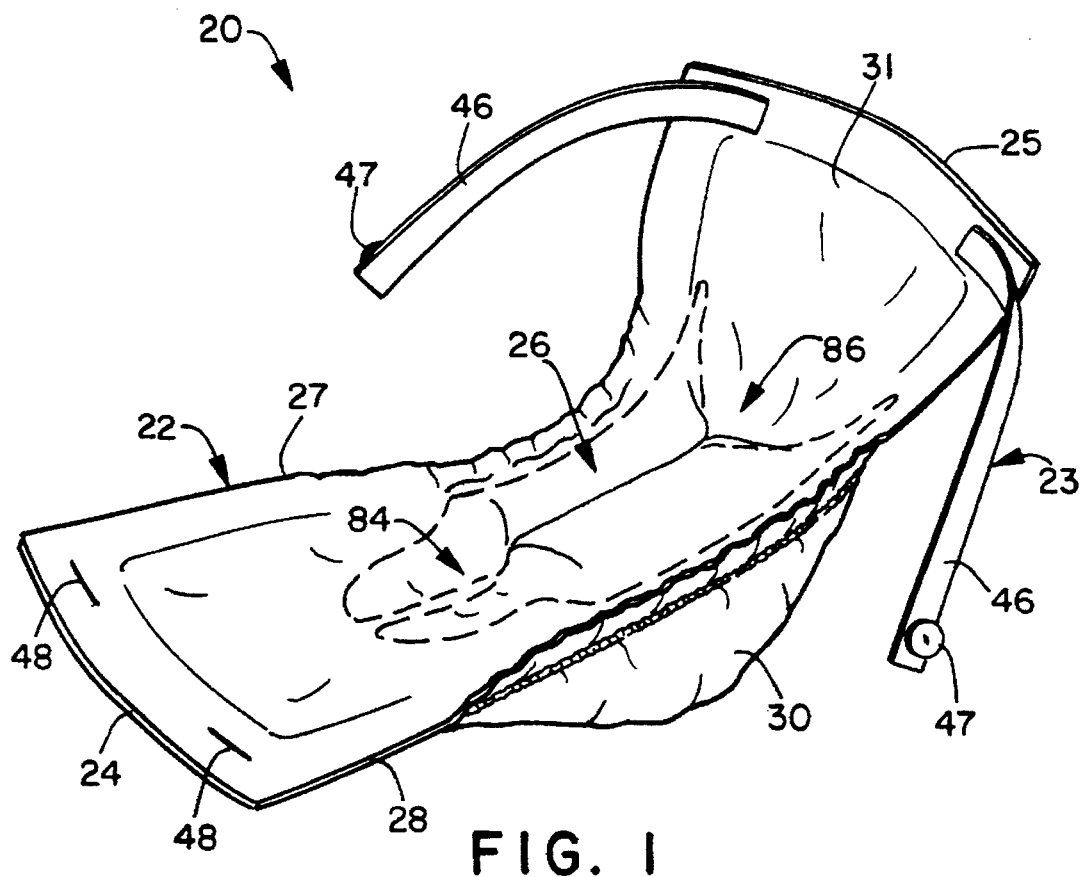
FIG. 1 is a perspective view of a shaped absorbent garment according to the present invention.

With reference to FIG. 1, a disposable absorbent garment 20 according to the present invention is shown for purposes of illustration as an adult incontinence product. The invention may also be incorporated in other types of disposable absorbent garments, such as diapers, training pants or feminine care products. The illustrated disposable absorbent garment includes a folded garment shell 22 and an attachment system 23 for securing the shell to the body of a wearer. The shell 22 is folded and secured as described below to provide a snug fitting, comfortable absorbent garment that rapidly absorbs fluidic waste and efficiently contains fecal material. With additional reference to FIG. 2, where the garment shell 22 is shown in an unfolded and stretched condition, the shell has a front edge 24 and an opposite back edge 25 that is longitudinally spaced from the front edge. A crotch section 26 is located intermediate the front and back edges 24 and 25. First and second sides 27 and 28 of the shell 22 extend longitudinally between the front and back edges 24 and 25.

The shell 22 is illustrated as rectangular in shape, but may optionally be formed in other shapes, such as hourglass-shaped, I-shaped or T-shaped, and may have any suitable dimensions. For example, the length may be from about 18 to about 36 inches (ca. 46–92 cm), such as about 30 inches (ca. 76 cm) for an adult, and the width may be from about 6 to about 12 inches (ca. 15–31 cm), such as about 9 inches (ca. 23 cm) for an adult. The thickness of the shell 22 may be from about ¼ to about 2 inches (ca. 0.6–5 cm), such as about ½ inch (ca. 1.3 cm). Garments 20 may be sized to be worn inside of underwear.

The garment 20 also includes a backing sheet 30 (FIGS. 1, 3, 4 and 6–9) and an opposite bodyside liner 31 (FIGS. 1–8). Preferably, the backing sheet 30 is substantially liquid impermeable and the bodyside liner 31 is substantially liquid permeable. An absorbent core 34 (FIGS. 2–4 and 6–8) of the garment 20 is positioned between the backing sheet 30 and the bodyside liner 31. The backing sheet 30 and bodyside liner 31 are preferably longer and wider than the absorbent core 34, so that the peripheries of the backing sheet and bodyside liner form margins which may be sealed together using ultrasonic bonds, adhesives, or other suitable means. The absorbent core 34 is preferably although not necessarily, additionally secured to the backing sheet 30 and the bodyside liner 31 using dots or lines of adhesives, ultrasonic bonds, or other suitable means.

A wide variety of materials may be used to construct the aforementioned components of the garment 20. The backing sheet 30, for example, may comprise a thin, substantially liquid impermeable web or sheet of plastic film such as polyethylene, polypropylene, polyvinyl chloride or similar material. The backing sheet material may be transparent or opaque and have an embossed or matte surface. One preferred material for the backing sheet 30 is a polyethylene film that has a nominal thickness of about 0.001 inch and a systematic matte embossed pattern, and that has been corona treated on both sides. Alternately, the backing sheet 30 may comprise a nonwoven, fibrous web which has been suitably constructed and arranged to be substantially liquid impermeable.

The bodyside liner 31 may be any soft, flexible, porous sheet which passes fluids therethrough. The bodyside liner 31 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The bodyside liner 31 has a pore size that readily allows the passage therethrough of liquids, such as urine and other body exudates. The liner 31 may be selectively embossed or perforated with discrete slits or holes extending therethrough. Optionally the web or sheet may be treated with a surfactant to aid in liquid transfer. One preferred bodyside liner material is a wettable spunbonded polypropylene having a basis weight of about 0.7 ounces per square yard. Such material may be produced by the methods and apparatus described in U.S. Pat. Nos. 4,340,563 and 4,405,297 to Appel et al., which are incorporated herein by reference to the extent that they are consistent herewith.

Figure 2:
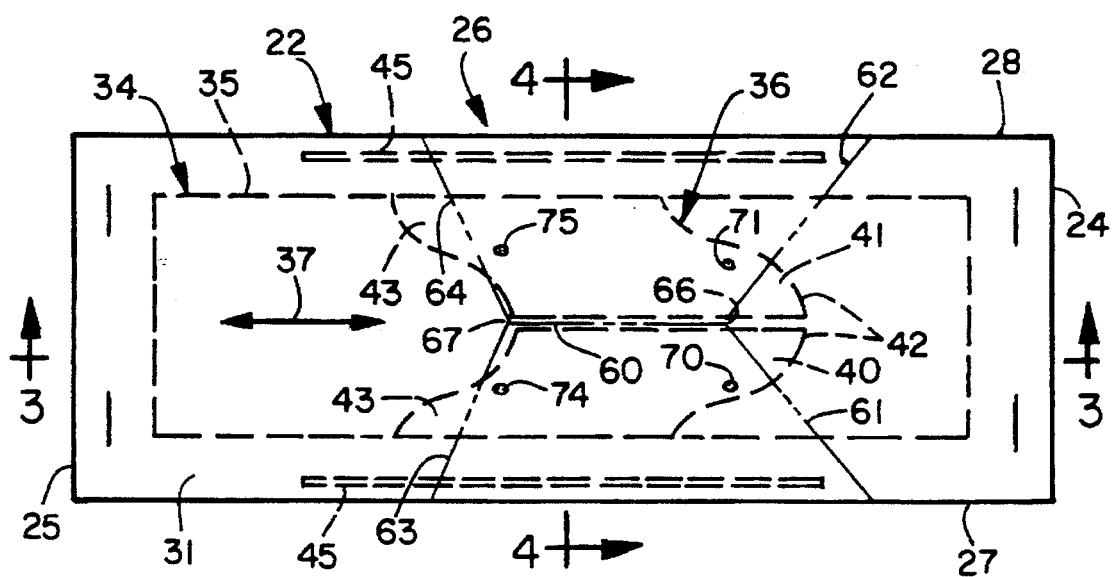
FIG. 2 is a top plan view of a shell of the shaped garment of FIG. 1, excluding elements of the garment attachment system, with the front/back orientation of the garment being reversed as compared to FIG. 1 and the shell being shown prior to folding and in a stretched condition.
Figure 3:
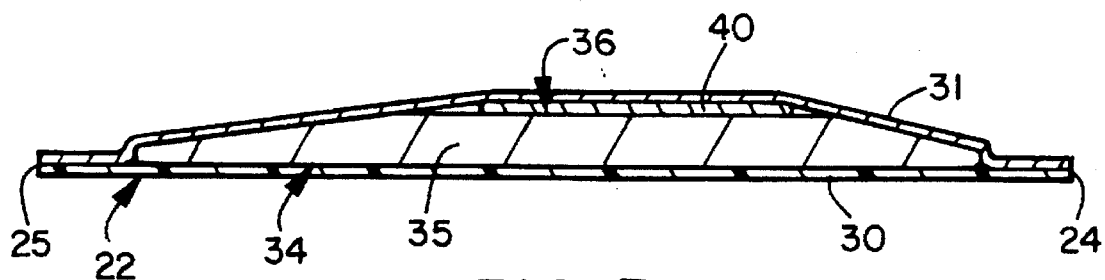
FIG. 3 is a view in section taken generally from the plane of the line 3—3 of FIG. 2.
Figure 4:
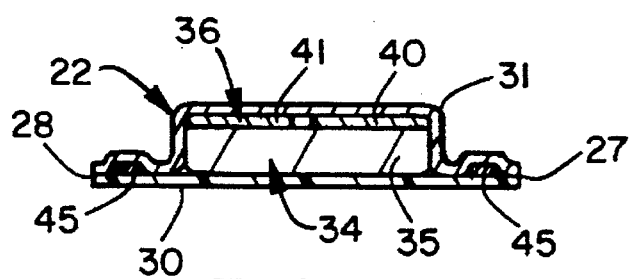
FIG. 4 is a view in section taken generally from the plane of the line 4—4 of FIG. 2.

The absorbent core 34 preferably, although not necessarily, comprises a storage layer 35 and an acquisition or distribution layer 36 (FIGS. 2–8). The dimensions of the absorbent core 34 may vary considerably. The length and width of the absorbent core 34 are preferably smaller than the length and width of the backing sheet 30 and the bodyside liner 31, while the thickness of the absorbent core 34 may be from about ⅛ to about 1-¾ inches (ca. 0.3–4 cm), such as about ⅜ inch (ca. 1 cm). The storage layer 35 is shown as rectangular, but may be formed in other shapes such as irregular, hourglass-shaped, I-shaped or T-shaped. The shell 22 has a central, longitudinal axis that lies generally in the plane of the storage layer 35 and is represented in FIG. 2 by arrow 37. The transverse axis of the shell 22 lies generally in the plane of the storage layer 35 and is perpendicular to the central, longitudinal axis. The storage layer 35 is preferably, although not necessarily, evenly spaced transversely between the first and second sides 27 and 28 and longitudinally between the front and back edges 24 and 25.

The storage layer 35 is preferably an air-formed batt of cellulosic fibers (i.e., wood pulp fluff). Suitable types of wood pulp fluff are available from Kimberly-Clark Corporation of Neenah, Wis. Optionally, the storage layer 35 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The storage layer 35 may also include compounds to increase its absorbency, such as an effective amount of organic or inorganic high-absorbency materials. For example, the storage layer 35 can include 0–95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Celanese Corporation, and Allied-Colloid. Typically, the high-absorbency material is capable of absorbing at least about 15 times its weight in water, and preferably is capable of absorbing more than about 25 times its weight in water.

The high-absorbency material can be distributed or otherwise incorporated into the storage layer 35 employing various techniques. For example, the high-absorbency material can be substantially uniformly distributed among the fibers comprising the storage layer. The materials can also be nonuniformly distributed within the storage layer fibers to form a generally continuous gradient with either an increasing or decreasing concentration of high-absorbency material, as determined by observing the concentration moving inward from the backing sheet 30. Alternatively, the high-absorbency material can comprise a discrete layer separate from the fibrous material of the storage layer 35, or can comprise a discrete layer integral with the storage layer.

The storage layer 35 may have a density, for example, from about 0.05 to about 0.3 grams per cubic centimeter, and more particularly from about 0.05 to about 0.2 grams per cubic centimeter. The storage layer 35 is sufficiently flexible to readily conform to the body of the wearer and to be folded and secured as hereinafter described. The storage layer 35 can optionally include a substantially hydrophilic tissue wrap (not shown) to help maintain the integrity of the fibrous structure. The tissue wrap sheet typically comprises an absorbent cellulosic material, such as creped wadding or a high wet-strength tissue.

The acquisition or distribution layer 36 of the absorbent core 34 preferably comprises a pair of surge or transfer sheets 40 and 41, which are preferably positioned between the storage layer 35 and the bodyside liner 31. The surge sheets 40 and 41 are preferably secured to both the storage layer 35 and the bodyside liner 31 using dots or lines of adhesive, ultrasonic bonds or other suitable means. Optionally, the surge sheets 40 and 41 could be secured to either the storage layer 35 or the bodyside liner 31. The preferred shape of the surge sheets 40 and 41, which are identically formed, is best illustrated in FIG. 2. The surge sheets 40 and 41 are trapezoid-like in that they have two opposite parallel sides and two opposite curved sides. The curved sides are complementary, so that numerous shaped surge sheets 40 and 41 may be cut from a length o material with minimum waste. The opposite, parallel (straight) sides are desirably about 7 inches (ca. 18 cm) in length, spaced apart from one another by about 3.25 inches (ca. 8 cm), and longitudinally offset from one another by about 3.5 inches (ca. 9 cm).

The surge sheets 40 and 41 are positioned adjacent one another in the crotch section 26 on opposite sides of the central, longitudinal axis of the shell 22. The two opposite parallel sides are positioned parallel to the central, longitudinal axis. As illustrated, the surge sheets 40 and 41 each have a leading section 42 adjacent the central, longitudinal axis and extending toward the front edge 24. Each surge sheet 40 and 41 also has a trailing section 43 extending toward the back edge 25. The trailing section 43 for surge sheet 40 is positioned adjacent the first side 27, and the trailing section 43 for surge sheet 41 is positioned adjacent the second side 28. Considering each surge sheet to have four sides two straight and two curved, the leading section 42 is located diagonally from the trailing section 43. Optionally, a single surge sheet (not shown) could be used instead of two separate sheets, although two sheets are preferred so that the vertical surge material is not doubled up along the central, longitudinal fold in the crotch section 26.

The surge sheets 40 and 41 can be or can contain any suitable material for managing, accommodating, permitting, or directing rapid and/or sudden flow of urine and/or other excreted or discharged liquid therethrough and into contact with the storage layer 35. The surge sheets 40 and 41, which are relatively resilient, support the garment 20 when it is folded and help to retain its absorbent integrity when compressed during wear. The surge sheets 40 and 41 are illustrated in FIGS. 1–9 as being positioned between the bodyside liner 31 and the storage layer 35, although the surge sheets may also be positioned on the surface of the bodyside liner that is remote from the storage layer. In either location, the surge sheets 40 and 41 separate the wearer's skin from the storage layer 35 to thereby provide a cooler, drier surface against the skin.

The surge sheets 40 and 41 preferably have a substantially uniform density throughout and have an essentially or generally nonlayered configuration. The density can be from about 0.015 to about 0.5 grams per cubic centimeter. The surge sheets may have a fiber denier from about 1.5 to about 15, and particularly from about 1.5 to about 6. The surge sheets 40 and 41 may also have a pore size gradient therein, for instance, as having a series of stratified zones, or may have a substantially uniform porosity. When positioned below the bodyside liner 31, the surge sheets should have a pore size smaller than that of the liner but larger than that of the storage layer 35 upon which it resides. In that manner a stepwise gradient is formed among the components of the garment 20. Thus, provided is a preferential flow direction away from the body of the wearer, away from the components of the garment nearest the wearer, and into the storage layer 35. Consequently, flowback of liquids is reduced and restricted to provide a drier product.

The resiliency of surge sheets 40 and 41 is generally such that the resultant pore size gradient is substantially maintained during ordinary use of the garment 20 by the wearer. Thus, this configuration is constructed to be resiliently compressible during ordinary use. Upon such compression, representable as a pressure about from 0.2 to 0.5 pounds per square inch (ca. 1.38–3.45 kPa), the effective pore size therein remains larger than that of the immediately adjacent portion of storage layer 35, and if covered by the bodyside liner 31, remains preferably less than that of the bodyside liner. When compression of the surge sheets 40 and 41 is released, the sheets can re-expand to provide a larger effective pore size and an increased surge capacity. Preferably, the pore size gradient and re-expansion capability are maintained in the surge sheets 40 and 41 even when they are wet.

To maintain the desired effectiveness of the surge sheets 40 and 41, they should be able to generally maintain their occupied space wet or dry. Accordingly, the wet and dry compression recovery values of the surge sheets should be at least about 65 percent, preferably at least about 80 percent, and more preferably at least about 95 percent. The compression recovery value (CRV) is a measure of the resiliency of the material and is determined by measuring the original thickness (To) of the material under a restraining pressure of 0.068 pounds per square inch (0.47 kPa). The material is then subjected to a compression force of 0.5 pounds per square inch (3.45 kPa). The compression force is then removed, and the recovery thickness (Tr) of the material is measured under the original restraining pressure. The compression recovery value is then determined in accordance with the formula: $CRV=(Tr/To)\times(100\%)$. When this determination is made employing a dry surge sheet 40 and 41, the dry CRV is obtained. When this determination is made employing a surge sheet 40 and 41 substantially saturated with distilled water, the wet CRV is obtained.

Included among suitable components for surge sheets 40 and 41 are substantially hydrophobic transport materials such as nonwoven polypropylene, polyethylene, polyester, blends thereof, and the like. One suitable material, which is identified as SH-66 and available from Sackner Products of Grand Rapids, Mich., is a latex bonded polyester. The material may have a thickness from about ⅛ to about ½ inch (ca. 0.3–1.3 cm), such as about ¼ inch (ca. 0.6 cm), for example, and a density of about 0.022 grams per cubic centimeter uncompressed.

The surge sheets 40 and 41 may contain or be treated with a suitable surfactant to increase their initial wettability in adjustment of the performance of this invention. When treated with a surfactant, however, the surge sheets 40 and 41 should still be less hydrophilic than the storage layer 35. The presence of an effective amount of surfactant on the surge sheets 40 and 41 can advantageously increase the rate of movement of liquid into the storage layer 35 during initial insult or discharge of liquid into the garment 20. After the initial insult, however, bodily discharges such as urine will continue to move through the surge Sheets 40 and 41 whether or not the surfactant is present therein. Accordingly, the surfactant may be water dispersible, if desired. Various surfactants are available, as is known in the art. For example, one suitable surfactant is identified as Triton X-102 and is available from Rohm and Haas Corporation of Philadelphia, Pa.

The garment 20 may also include elastic strands or ribbons 45 (FIGS. 2, 4 and 6–9) longitudinally orientated along each side margin of the garment 20, adjacent the first and second sides 27 and 28. The elastic strands 45 are located in the crotch section 26 and extend toward the front and back edges 24 and 25. The strands 45 are secured in an extended condition preferably to both the bodyside liner 31 and the backing sheet 30. The elastic strands 45 form seals or gaskets about the leg of the wearer.

The elastic strands 45 may be formed a dry-spun coalesced multifilament elastomeric thread sold under the tradename LYCRA and available from I.E. Du Pont de Nemours and Company. Alternately, the elastic strands may be formed of other typical elastics utilized in the diaper-making art, such as a thin ribbon of natural rubber. Elasticity could also be imparted to the longitudinal side margins by extruding a hot melt elastomeric adhesive between the backing sheet 30 and the bodyside liner 31. Other suitable elastic gathering means are disclosed in U.S. Pat. Nos. 4,938,754 to Mesek and 4,388,075 to Mesek et al.

The attachment system 23 (FIG. 1) of the garment 20 as illustrated includes a pair of straps 46. Each strap 46 carries a retainer 47 at each opposite end thereof. The retainers 47 may be releasably secured in slits 48 formed in the backing sheet 30 and bodyside liner 31, near the four corners of the shell 22. When the garment 20 is positioned on the wearer, the straps 46 extend between the front and back slits 48 so that the retainers 47 may be releasably secured in the slits. This attachment system 23 is described in U.S. Pat. No. 4,315,508 to Bolick, which is incorporated herein by reference to the extent that it is consistent herewith. Optionally, other types of attachment systems, such as tapes, stretchable side panels, or hook-and-loop fasteners (not shown), may be employed.

The folded absorbent garment 20 is preferably constructed by folding the shell 22 along a series of score or fold lines, as illustrated by phantom lines 60–64 in FIG. 2. Initially, the shell 22 is inwardly folded along fold line 60. Optionally, rather than folding all components of the shell 22, it will be appreciated that only the absorbent core 34, or the absorbent core 34 and the bodyside liner 31, could be folded as herein disclosed. Fold line 60 generally corresponds to the central, longitudinal axis of the shell 22 between a forward terminal point 66 and a rearward terminal point 67.

The forward and rearward terminal points 66 and 67 are spaced apart and generally positioned o the central longitudinal axis. The forward terminal point 66 defines the forward extent of the crotch section 26, and the rearward terminal point 67 defines the rearward extent of the crotch section. The terminal points 66 and 67 of the central, longitudinal fold 60 are preferably positioned so that the fold is formed generally beneath the perineal area, for both male and female wearers of the garment. For females, the fold 60 can be located directly beneath the urethra. Preferably although not necessarily, the surge sheets 40 and 41 are longitudinally positioned so that the leading sections 42 extend forward of the forward terminal point 66, and the trailing sections 43 extend rearward of the rearward terminal point 67. The forward and rearward terminal points 66 and 67 are preferably spaced apart from about 0.25 to about 6.0 inches, and more preferably from about 1.5 to about 4.0 inches.

The shell 22 is also inwardly folded along a pair of forward diverging fold lines 61 and 62, which originate at the forward terminal point 66 and extend toward the first and second sides 27 and 28. Specifically, fold line 61 extends from the forward terminal point 66 toward the longitudinally-extending side of the absorbent core 34 that is adjacent the first side 27. Fold line 62 extends from the forward terminal point 66 toward the longitudinally-extending side of the absorbent core 34 that is adjacent the second side 28. The diverging fold lines 61 and 62 are considered to extend forward, because they intersect the longitudinally-extending sides of the absorbent core 34 at a longitudinal position which is intermediate the forward terminal point 66 and the front edge 24.

The forward diverging fold lines 61 and 62 each form an angle with the central, longitudinal axis that is preferably from about 30 to about 70 degrees, and more preferably from about 40 to about 60 degrees, such as the angle of approximately 50 degrees illustrated in FIG. 2.

Furthermore, the shell 22 is inwardly folded along a pair of rearward diverging fold lines 63 and 64, which originate at the rearward terminal point 67 and extend toward the first and second sides 27 and 28. More specifically, fold line 63 extends from the rearward terminal point 67 toward the longitudinally-extending side of the absorbent core 34 that is adjacent the first side 27, and fold line 64 extends from the rearward terminal point 67 toward the longitudinally-extending side of the absorbent core 34 that is adjacent the second side 28. The diverging fold lines 63 and 64 are considered to extend rearward, because they intersect the longitudinally-extending sides of the absorbent core 34 at a longitudinal position which is intermediate the rearward terminal point 67 and the back edge 25.

The rearward diverging fold lines 63 and 64 each form an angle with the central, longitudinal axis that is preferably from about 40 to about 80 degrees, and more preferably from about 55 to about 75 degrees, such as the angle of approximately 65 degrees illustrated in FIG. 2. Preferably, the angle formed between the rearward diverging fold lines 63 and 64 and the central, longitudinal axis is greater than the angle formed between the forward diverging fold lines 61 and 62 and the central, longitudinal axis. The foregoing cited preferred angles for the forward and rearward diverging fold lines 61–64 provide a body-conforming and comfortable fit to reduce the potential for leakage in adult incontinence products. Because the forward and rearward diverging fold lines are preferably different, it may be desirable for the garment shell 22 to include a front or a back indicator (not shown), such as a visual indicator.

The garment 20 is maintained in a folded shape by securing particular points or areas on one side of the central, longitudinal axis to particular points or areas on the other side. For purposes of illustration and description, these points or areas will be referred to as contact points or areas. With reference to FIG. 2, a first forward contact point 70 is generally located transversely outward from the forward terminal point 66. As illustrated, the first forward contact point 70 is located approximately midway between the central, longitudinal axis and the first side 27 of the shell 22. A second forward contact point 71 is generally located transversely outward from the forward terminal point 66, approximately midway between the central, longitudinal axis and the second side 28. Similarly, first and second rearward contact points 74 and 75 are generally located transversely outward from the rearward terminal point 67. As illustrated, the first rearward contact point 74 is located approximately midway between the central, longitudinal axis and the first side 27, and the second rearward contact point 75 is located approximately midway between the central, longitudinal axis and the second side 28. Desirably, the forward contact points 70 and 71 are spaced from the central, longitudinal axis by approximately the same amount that the rearward contact points 74 and 75 are spaced from the central, longitudinal axis.

After preferably folding the shell 22 as previously indicated, the first and second forward contact points 70 and 71 are secured together using construction adhesives, ultrasonic bonds, stitches, or other suitable means readily known to those skilled in the art. Because the storage layer 35, acquisition layer 36 and bodyside liner 31 are preferably secured to one another, connecting these contact points 70 and 71 causes the portions of the storage layer 35, which correspond to the contact points 70 and 71, to be indirectly joined together. In a similar manner, the first and second rearward contact points 74 and 75 are also secured together. Optionally, of course, if the storage layer 35, acquisition layer 36 and bodyside liner 31 were not directly secured to one another, these components could be bonded together at least in the general vicinity of the contact points 70, 71, 74 and 75, to accomplish the same result.

It will be appreciated that other means of securing the portions from opposite sides of the central, longitudinal axis are possible. For example, a series of adhesive dots may be applied between the first contact points 70 and 74 or between the second contact points 71 and 75. Optionally, a series of adhesive dots may be applied between the forward contact points 70 and 71 and between the rearward contact points 74 and 75. Still optionally, a light spray of adhesive may be applied to the entire area of the shell 22 defined within the contact points 70, 71, 74 and 75, or applied to the area on one side of the central, longitudinal axis and inboard of either the first or second set of contact points 70 and 74 or 71 and 75. A light spray pattern of adhesive has been found to not substantially inhibit downward fluid flow in the garment, whereas longitudinally-extending lines of adhesive may inhibit such fluid transport.

It will also be appreciated that, although it is preferred that the contact points or areas lie in the crotch section 26, the contact points or areas need not longitudinally correspond exactly with the forward and rearward terminal points 66 and 67. Also, as illustrated hereinafter in another embodiment, the contact points or areas may extend transversely either a greater extent or a lesser extent from the central, longitudinal axis.

With reference to FIGS. 1 and 5–8, the crotch section 26 of the resulting shaped absorbent garment 20 is relatively narrow and includes a vertically-extending channel 80. The crotch section 26 tends to fit snugly and comfortably against the body of the wearer. As seen best in FIG. 7, the channel 80 is formed by portions of the bodyside liner 31, surge sheets 40 and 41 and storage layer 35 from opposite sides of the central, longitudinal axis, which portions are illustrated as being joined together by securement means 81. The securement means 81 may be an adhesive bond, an ultrasonic bond, a stitch, or any other suitable bond for joining the portions together. The position of the securement means 81 corresponds generally to that of the contact points 70, 71, 74 and 75 (FIG. 2), or the contact area defined thereby. The portions of the bodyside liner 31 and surge sheets 40 and 41 that form the channel 80 function to rapidly absorb and transport liquid waste away from the wearer. The liquid is transported toward the deepest part of the crotch section 26 where it may be desorbed into and retained by the storage layer 35.

Between the crotch section 26 and the front edge 24, the shaped absorbent garment 20 includes a front pocket 84. The front pocket 84 beneficially accommodates the genitals of male wearers or comfortably collapses inwardly against the body of female wearers. As shown best in FIGS. 5 and 6, the front pocket 84 includes the leading sections 42 of the surge sheets 40 and 41. These leading sections 42 provide an especially dry environment by transporting liquid waste away from the wearer.

Figure 5:
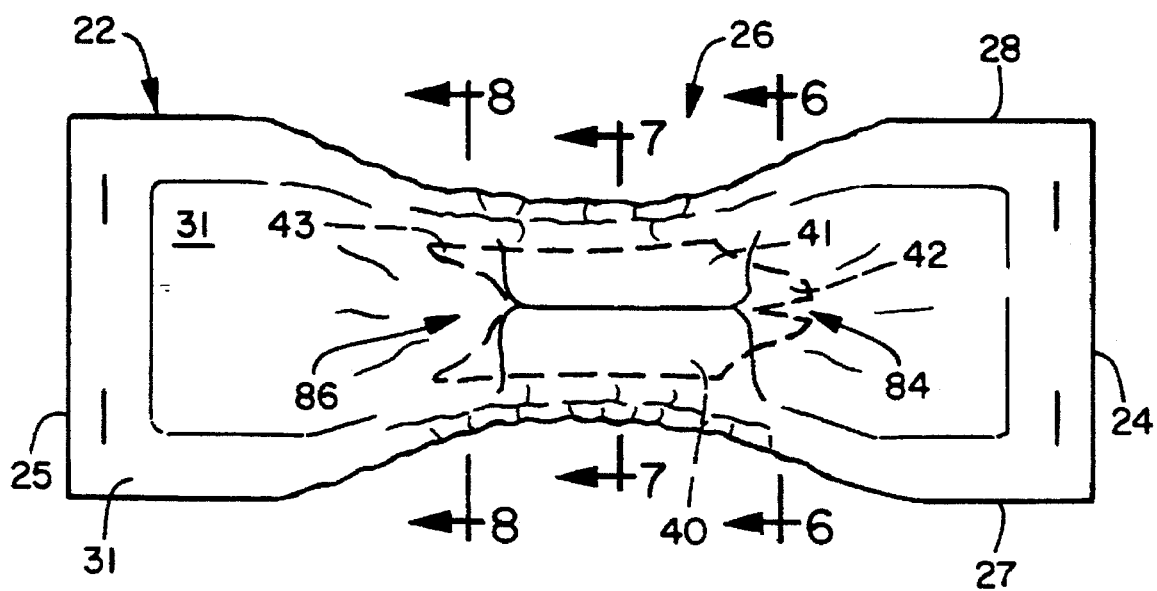
FIG. 5 is a top plan view of the shaped garment of FIG. 1, but excluding elements of the garment attachment system.
Figure 6:
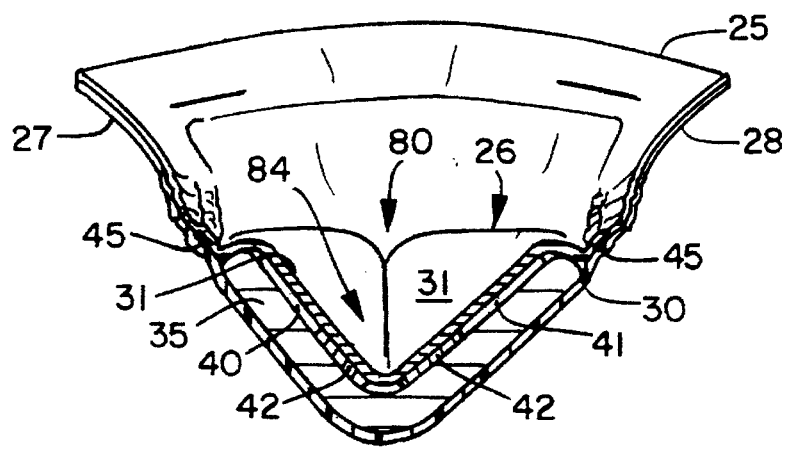
FIG. 6 is a view in section taken generally from the plane of the line 6—6 of FIG. 5.
Figure 7:
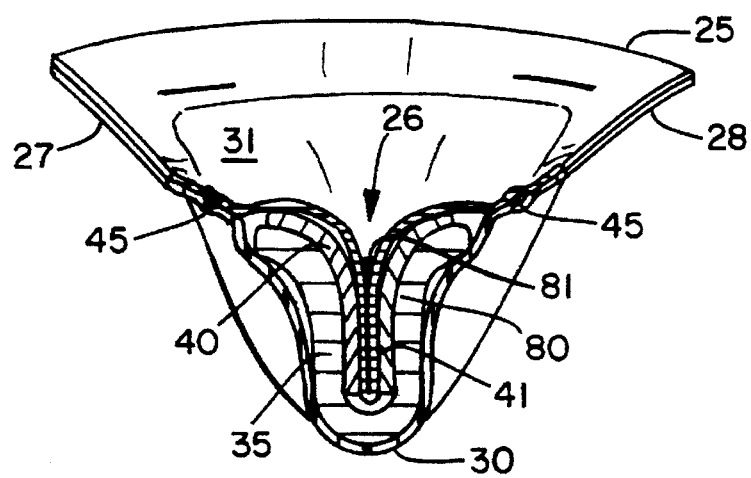
FIG. 7 is a view in section taken generally from the plane of the line 7—7 of FIG. 5.
Figure 8:
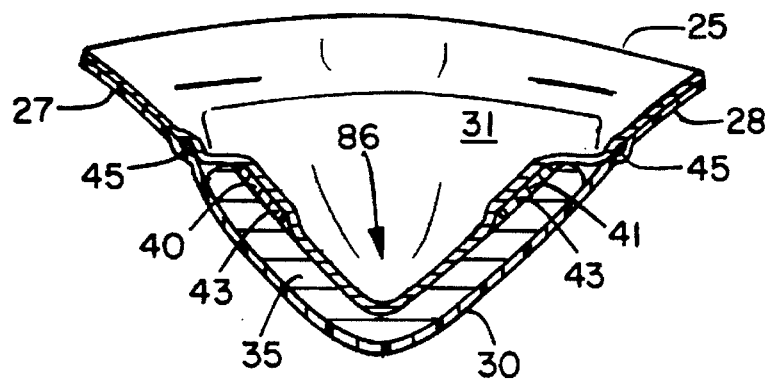
FIG. 8 is a view in section taken generally from the plane of the line 8—8 of FIG. 5.
Figure 9:
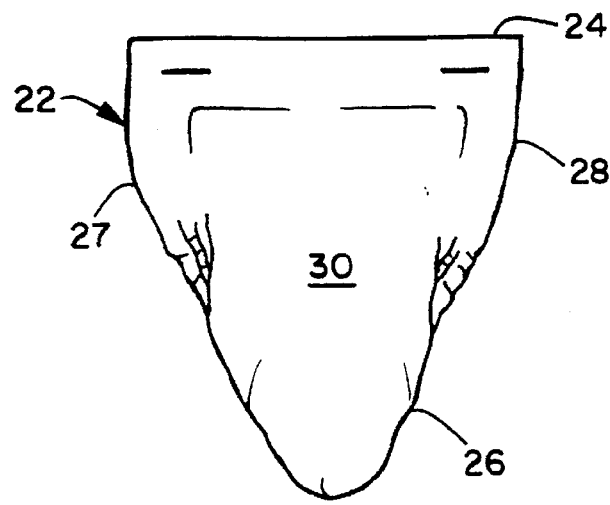
FIG. 9 is a front plan view of the shaped garment of FIG. 1, but excluding elements of the garment attachment system.

The shaped absorbent garment 20 includes a rear pocket 86 between the crotch section 26 and the back edge 25. The rear pocket 86 is positioned to accommodate and subsequently retain fecal waste. The trailing sections 43 of the surge sheets 40 and 41 are positioned adjacent the rear pocket 86. Thus, as best shown in FIGS. 5 and 8, surge material is not located in the base of the rear pocket 86 where it generally would not be necessary, and would disadvantageously decrease the volume thereof. The trailing sections 43, positioned adjacent the rear pocket 86 and adjacent the longitudinally-extending sides of the storage layer 35, are desirable, however, to reduce the possibility of leakage due to fluid migrating toward the sides of the garment during wear. Additionally, the positioning of the trailing sections 43 is especially advantageous for female wearers, because the trailing sections tend to transport liquid waste rearward in the shell 22 to more fully utilize the absorbent capacity of the storage layer 35.

Figure 10:
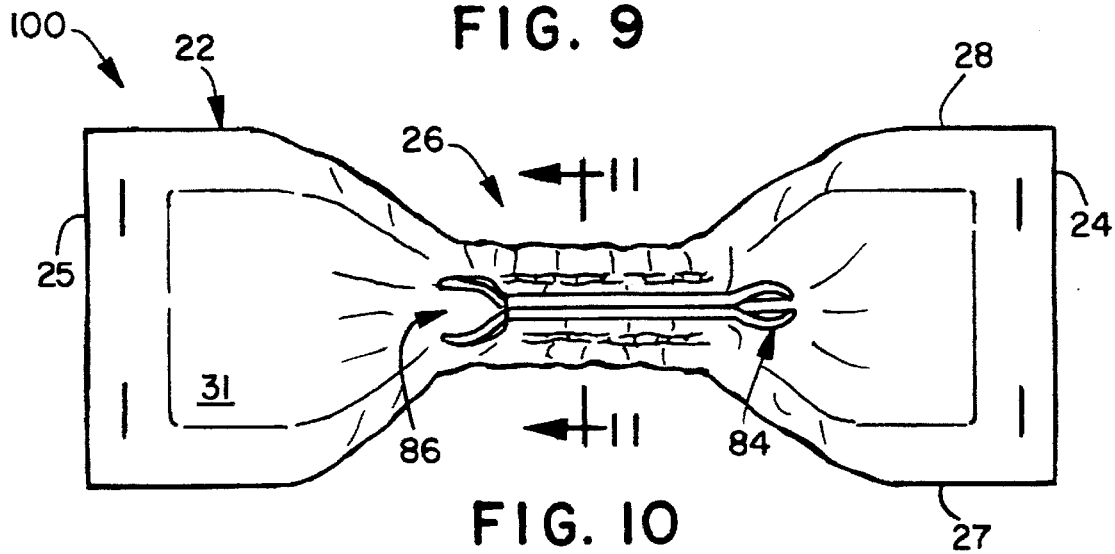
FIG. 10 is a top plan view of a shell of another embodiment of a shaped garment according to the present invention, excluding elements of the garment attachment system.
Figure 11:
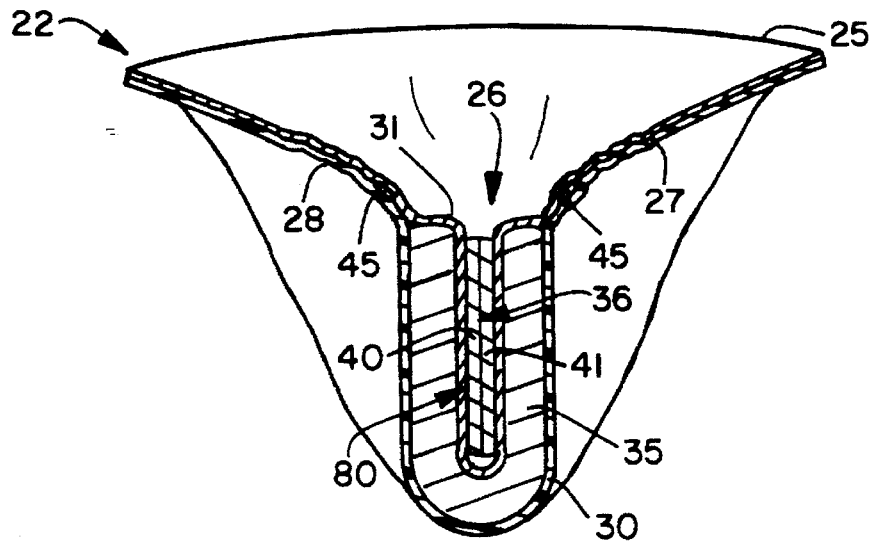
FIG. 11 is a view in section taken generally from the plane of the line 11—11 of FIG. 10.

A second embodiment of the present invention is illustrated by the shaped absorbent garment 100 of FIGS. 10 and 11. Components similar to those previously described are labeled with the same reference numeral. The shaped absorbent garment 100 includes a shell 22 with a front edge 24, an opposite back edge 25 longitudinally spaced from the front edge, and a narrow crotch section 26 located intermediate the front and back edges 24 and 25. The shell 22 also includes first and second sides 27 and 28, a backing sheet 30, and a bodyside liner 31.

An absorbent storage layer 35 of the garment 100 is positioned between and preferably secured to the backing sheet 30 and the bodyside liner 31. An acquisition or distribution layer 36 is positioned on and secured to the bodyside liner 31 using adhesives, ultrasonic bonds or other suitable means. The acquisition layer 36 preferably comprises a pair of identical surge sheets 40 and 41, but may alternately comprise a single sheet of surge material. The surge sheets 40 and 41 are positioned adjacent one another in the crotch section 26 on opposite sides of the central, longitudinal axis of the shell 22.

The folded absorbent garment 100 is constructed by folding the shell 22 in the manner previously described in relation to the embodiment of FIGS. 1–9. The garment 100 is maintained in a folded shape by securing the surge sheets 40 and 41 in the crotch section 26 to one another, preferably with dots or a light spray pattern of adhesive. Specifically, the surface of the shell 22 in the crotch section and between the central, longitudinal axis and the longitudinally-extending side of the storage layer 35 adjacent the first side 27 is secured to the surface of the shell in the crotch section between the central, longitudinal axis and the longitudinally-extending side of the storage layer 35 adjacent the second side 28. Although not shown in FIGS. 10 and 11, it will be recognized that the contact points are located transversely outward from the central, longitudinal axis and generally adjacent the longitudinally-extending sides of the storage layer 35. Most preferably, the contact points are located transversely outward from the forward and rearward terminal points 66 and 67, such as shown in FIG. 2.

The garment 100 thereby has a narrow crotch section 26 with a vertically-extending channel 80 formed by the surge sheets 40 and 41, the bodyside liner 31 and the storage layer 35. A front pocket 84 is formed forward of the crotch section 26, and a rear pocket 86 is formed rearward of the crotch section. Due to the location of the contact points, the depth of the channel 80 is approximately equal to one half the width of the storage layer 35. This embodiment provides an especially deep channel 80, and especially deep front and rear pockets 84 and 86.

As can be appreciated by comparing the embodiment of FIGS. 1–9 with the embodiment of FIGS. 10–11, the distance of the securement means (see 81 in FIG. 7) from the central, longitudinal axis may be varied to alter the depth of the vertical channel 80 as well as the width of the crotch section 26. Thus for example, as the securement means is applied more toward the longitudinally-extending sides 27 and 28, the depth of the crotch section increases and the width of the crotch section, i.e., distance between the sides, decreases. Furthermore, as the securement means is applied more toward the longitudinally-extending sides 27 and 28, the depth of the front and rear pockets 84 and 86 becomes greater, with the terminal points 66 and 67 defining the deepest parts of the front and rear pockets.

Figure 12:
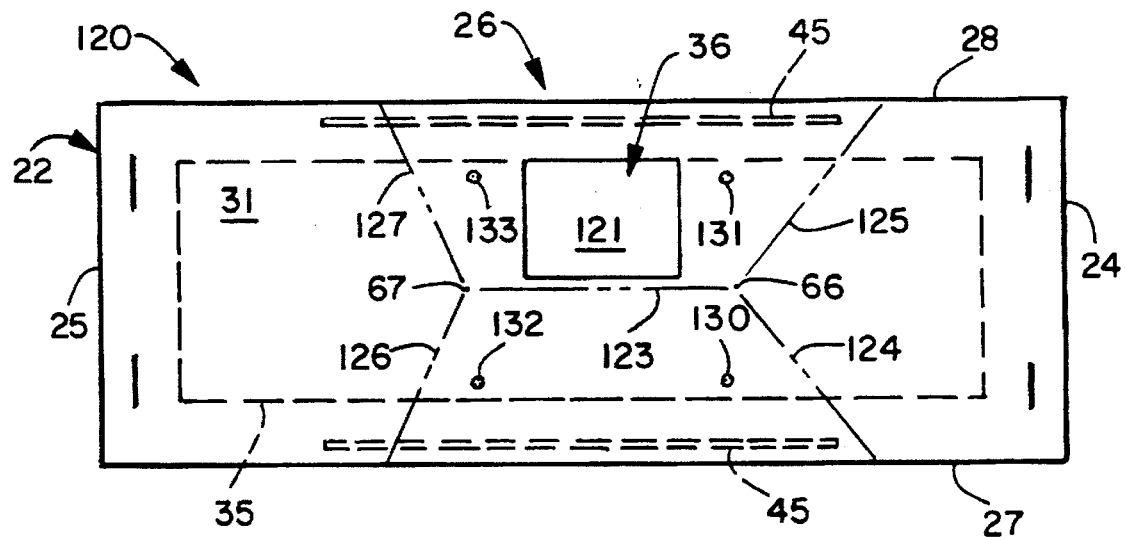
FIG. 12 is a top plan view of a shell of another embodiment of a shaped garment according to the present invention, the shell being shown prior to folding and in a stretched condition, and excluding elements of the garment attachment system.
Figure 13:
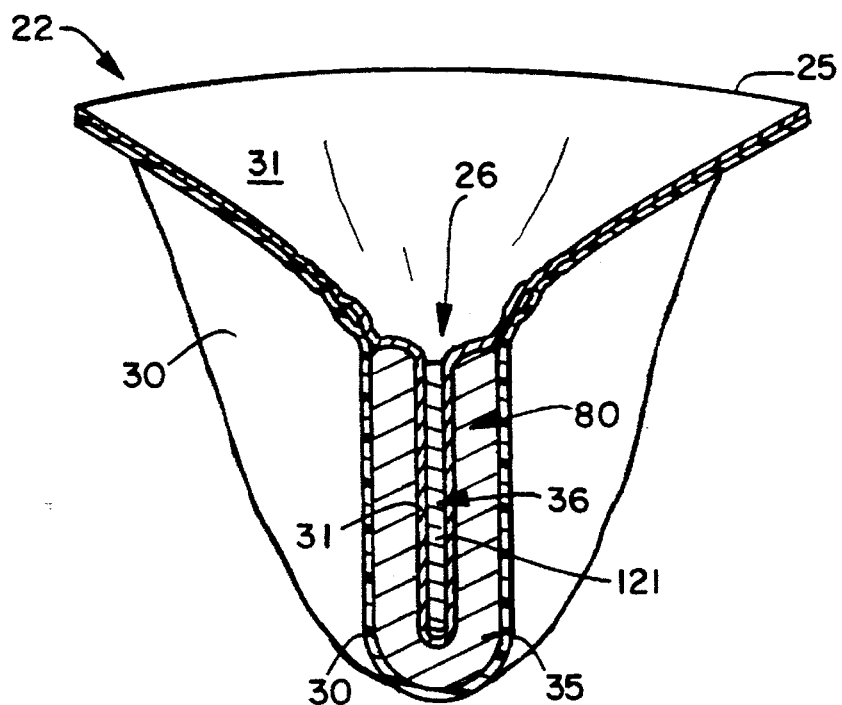
FIG. 13 is a view in section similar to FIG. 11, but relating to the shaped absorbent garment of FIG. 12.

Another embodiment of the present invention is illustrated by shaped absorbent garment 120 of FIGS. 12 and 13. As with other embodiments, this garment 120 includes a shell 22 with a front edge 24, an opposite back edge 25 longitudinally spaced from the front edge, and a narrow crotch section 26 located intermediate the front and back edges 24 and 25. The shell 22 also includes first and second sides 27 and 28, a backing sheet 30, and a bodyside liner 31. An absorbent storage layer 35 is positioned between and secured to the backing sheet 30 and the bodyside liner 31.

An acquisition or distribution layer 36 is positioned on and secured to the bodyside liner 31 using adhesives, ultrasonic bonds or other suitable means. In this embodiment, the acquisition layer 36 comprises a single, rectangular surge sheet 121 which is positioned on one side of the central, longitudinal axis of the shell 22. Optionally, the acquisition layer 36 may be positioned between the bodyside liner 31 and the storage layer 35 (not shown).

The folded absorbent garment 120 is constructed by inwardly folding the shell 22 along fold lines 123–127 (FIG. 12). Fold line 123 generally corresponds to the central, longitudinal axis of the shell 22 between a forward terminal point 66 and a rearward terminal point 67. Preferably although not necessarily, the surge sheet 121 is longitudinally centered between the forward and rearward terminal points 66 and 67. The forward and rearward terminal points 66 and 67 are preferably spaced apart from about 0.25 to about 6.0 inches, and more preferably from about 1.5 to about 4.0 inches.

The shell 22 is also inwardly folded along a pair of forward diverging fold lines 124 and 125, which originate at the forward terminal point 66 and extend toward the first and second sides 27 and 28. Similarly, the shell 22 is inwardly folded along a pair of rearward diverging fold lines 126 and 127, which originate at the rearward terminal point 67 and extend toward the first and second sides 27 and 28.

The preferred angles relative to the central, longitudinal axis for the forward and rearward diverging fold lines 124, 125, 126 and 127 are the same as previously mentioned. Optionally, of course, the angle formed between each of the diverging fold lines 124, 125, 126 and 127 and the central, longitudinal axis may be the same. In this case, the shell 22 would be symmetrical about the central, transverse axis.

The garment 20 is maintained in a folded shape by securing a first forward contact point 130 to a second forward contact point 131, and by securing a first rearward contact point 132 to a second rearward contact point 133. As illustrated, the first contact points 130 and 132 are located adjacent the longitudinally-extending side of the storage layer 35 that is adjacent the first side 27. The second contact points 131 and 133 are located adjacent the longitudinally-extending side of the storage layer 35 that is adjacent the second side 28. The first and second forward contact points 130 and 131 are preferably although not necessarily located transversely outward from the forward terminal point 66, and the first and second rearward contact points 132 and 133 are preferably although not necessarily located transversely outward from the rearward terminal point 67. In effect, similar to the embodiment of FIGS. 10 and 11, substantially the entire bodyside liner 31 in the crotch section 26 is folded along the central, longitudinal axis and secured onto itself, with the acquisition layer 36 therebetween.

With particular reference to FIG. 13, the resulting shaped absorbent garment 120 includes a narrow crotch section 26 with a vertically-extending channel 80, as well as front and rear pockets (not shown) adjacent either longitudinal end of the crotch section. In addition to the previously mentioned benefits of the present invention, this garment 120 is advantageous from a manufacturing perspective, because the acquisition layer 36 may be square or rectangular and positioned on the outwardly-directed surface of the bodyside liner 31. The garment 120 may also be formed to be symmetrical about the central, transverse axis, if desired.

The foregoing detailed description has been for the purpose of illustration. Thus, a number of modifications and changes may be made without departing from the spirit and scope of the present invention. For example, the absorbent core 34 alone may be folded and secured together, with the bodyside liner 31 therefore not forming any part of the vertically-extending channel 80. Also, the acquisition layer 36 may itself function as the bodyside liner. Likewise, the storage layer 35 or the acquisition layer 36 could be formed of multiple layers rather than a single layer as illustrated. Therefore, the invention should not be limited by the specific embodiments described, but only by the claims.

I claim:

1. A method of making a shaped absorbent garment, comprising the steps of:

providing a shell comprising a bodyside liner, a backing sheet, and an absorbent core, the absorbent core comprising a liquid storage layer positioned between the bodyside liner and the backing sheet, the shell having front and back edges and first and second sides extending between the front and back edges;

inwardly folding the shell along a central, longitudinal fold line, the central, longitudinal fold line having a forward terminal point and a rearward terminal point;

inwardly folding the shell along a pair of forward diverging fold lines that originate at the forward terminal point and extend toward the first and second sides;

inwardly folding the shell along a pair of rearward diverging fold lines that originate at the rearward terminal point and extend toward the first and second sides; and securing a first portion of the shell to a second portion of the shell, the first portion of the shell being defined by first forward and rearward contact points which are spaced from the central, longitudinal fold line and transversely located between the central, longitudinal fold line and the first side, the second portion of the shell being defined by second forward and rearward contact points which are spaced from the central, longitudinal fold line and transversely located between the central, longitudinal fold line and the second side.

2. The method of claim 1, wherein the forward and rearward terminal points are spaced apart from about 0.25 to about 6.0 inches.

3. The method of claim 1, wherein:

the first forward and rearward contact points are each transversely located adjacent a longitudinally-extending side of the absorbent core that is adjacent the first side; and the second forward and rearward contact points are each transversely located adjacent a longitudinally-extending side of the absorbent core that is adjacent the second side.

4. The method of claim 1, wherein the forward and rearward terminal points are spaced apart from about 1.5 to about 4.0 inches.

5. The method of claim 1, wherein the absorbent core comprises the storage layer and a single sheet of acquisition material, and the method further comprises positioning the single sheet of acquisition material on one side of the central, longitudinal fold line.

6. The method of claim 1, wherein the absorbent core comprises the storage layer and a pair of surge sheets, and the method further comprises positioning one surge sheet on each side of the central, longitudinal fold line.

7. The method of claim 6, wherein each surge sheet has a leading section located diagonally from a trailing section, and the method further comprises positioning the leading sections toward the front edge of the shell and adjacent the central, longitudinal fold line, and positioning the trailing sections toward the back edge of the shell.

8. The method of claim 7, wherein the leading sections extend forward of the forward terminal point, and the trailing sections extend rearward of the rearward terminal point.

9. The method of claim 6, wherein the surge sheets are identical in shape, each surge sheet having two opposite parallel sides and two opposite curved sides, the two opposite parallel sides being positioned parallel to the central, longitudinal fold line.

10. The method of claim 9, wherein the two opposite curved sides are complementary.

* * * * *